(12) United States Patent
Fujisaki et al.

(10) Patent No.: US 8,658,208 B2
(45) Date of Patent: *Feb. 25, 2014

(54) COATED SOLID PREPARATION

(75) Inventors: Yuki Fujisaki, Kamakura (JP); Ryoji Yoshii, Mishima (JP); Yasuhide Horiuchi, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/581,010

(22) PCT Filed: Feb. 25, 2011

(86) PCT No.: PCT/JP2011/054256
§ 371 (c)(1),
(2), (4) Date: Aug. 24, 2012

(87) PCT Pub. No.: WO2011/105539
PCT Pub. Date: Sep. 1, 2011

(65) Prior Publication Data
US 2012/0321677 A1 Dec. 20, 2012

(30) Foreign Application Priority Data
Feb. 26, 2010 (JP) ................................. 2010-042066

(51) Int. Cl.
| *A61K 9/32* | (2006.01) |
| *A61K 31/47* | (2006.01) |
| *A61P 11/00* | (2006.01) |
| *A61P 11/02* | (2006.01) |
| *A61P 11/06* | (2006.01) |

(52) U.S. Cl.
USPC ........................... 424/482; 424/474; 514/311

(58) Field of Classification Search
USPC .......................... 424/464, 474, 482; 514/311
See application file for complete search history.

(56) References Cited

U.S. PATENT DOCUMENTS

| 5,773,031 | A | 6/1998 | Shah et al. |
| 6,495,163 | B1 * | 12/2002 | Jordan ........................... 424/474 |
| 7,160,558 | B2 | 1/2007 | Petereit et al. |
| 2004/0241287 | A1 * | 12/2004 | Bastiaans et al. ............... 426/89 |
| 2011/0256189 | A1 * | 10/2011 | Hayashi et al. ............... 424/400 |

FOREIGN PATENT DOCUMENTS

| EP | 1985585 | * 10/2008 | .............. C01B 33/44 |
| JP | 179190 C2 | 6/1949 | |
| JP | 59-042325 A | 3/1984 | |
| JP | 61-186313 A | 8/1986 | |
| JP | 03-120211 A | 5/1991 | |

(Continued)

OTHER PUBLICATIONS

Nishioka et al., "Information on the stability of tablets and capsules in unpacked condition," (6th revised edition) Iyaku (Medicine and Drug) Journal Co., Ltd., 2009, p. 237 (with translation).

*Primary Examiner* — Rachael E Bredefeld
(74) *Attorney, Agent, or Firm* — DLA Piper LLP (US)

(57) ABSTRACT

A montelukast-containing coated solid preparation can be applied to one-dose package, wherein the humidity stability of montelukast or a pharmacologically acceptable salt thereof contained therein is maintained even when the preparation is unpacked. A coated solid preparation contains as an active ingredient montelukast or a pharmacologically acceptable salt thereof and is coated with a coating layer comprising polyvinyl alcohol and swelling clay, wherein the mass ratio of the above-described polyvinyl alcohol to the above-described swelling clay in the above-described coating layer is 8:2 to 3:7.

4 Claims, 6 Drawing Sheets

S1.03.008k.tif
Print Mag: 68000x @ 7.0 in
500 nm
HV=300kV
Direct Mag: 8000x

(56) References Cited

FOREIGN PATENT DOCUMENTS

| JP | 10-029936 A | 2/1998 |
| JP | 2004-518750 A | 6/2004 |
| JP | 2007-508271 A | 4/2007 |
| JP | 2007-145717 A | 6/2007 |
| JP | 2007-520546 A | 7/2007 |
| WO | 95/23594 A1 | 9/1995 |
| WO | 2005/040123 A1 | 5/2005 |
| WO | 2005/074893 A1 | 8/2005 |
| WO | 2008/142572 A2 | 11/2008 |
| WO | 2010/074223 A1 | 7/2010 |
| WO | 2010/110018 A1 | 9/2010 |

* cited by examiner

COATED SOLID PREPARATION

RELATED APPLICATIONS

This is a §371 of International Application No. PCT/JP2011/054256, with an international filing date of Feb. 25, 2011 (WO 2011/105539 A1, published Sep. 1, 2011), which is based on Japanese Patent Application No. 2010-042066, filed Feb. 26, 2010, the subject matter of which is incorporated by reference.

TECHNICAL FIELD

This disclosure relates to a coated solid preparation.

BACKGROUND

Leukotriene is a lipid mediator produced from arachidonic acid by 5-lipoxygenase and involved in inflammation and contraction of airway muscle and decrease/accumulation of the fluid amount in lung. Leukotriene C4, D4, and E4, which contain cysteine in their molecules, are called cysteinyl leukotriene, and cysteinyl leukotriene 1 (hereinafter referred to as "CysLT1") receptor and cysteinyl leukotriene 2 (hereinafter referred to as "CysLT2") receptor are known as a receptor thereof. CysLT 1 receptors and CysLT2 receptors, both of which are expressed in mastocytes, eosinophils, and endothelial cells, induce inflammation in endothelial cells under the stimulus of cysteinyl leukotriene, provide stimulation of chemokine production by mast cells, and are responsible for causing bronchial asthma and inflammatory disease.

Montelukast is an orally-active leukotriene receptor antagonist that selectively inhibits CysLT1 receptors. Sodium salts of montelukast (hereinafter referred to as "montelukast sodium") have been used as a useful therapeutic agent for respiratory disease, asthma, and allergic rhinitis. However, montelukast sodium has very high hygroscopicity, and it has been reported that Singulair (registered trademark) tablets and Kipres (registered trademark) tablets, which are commercially available as a pharmaceutical, have a problem in that they cause delayed disintegration and delayed dissolution due to moisture absorption upon storage for 4 weeks under conditions of 25° C. and a relative humidity of 85% (hereinafter referred to as "85% RH") ("Information on the stability of tablets and capsules in unpacked condition," (6th revised edition), Nishioka et al., Iyaku (Medicine and Drug) Journal Co., Ltd., 2009, p. 237).

As a method of improving the hygroscopicity of montelukast sodium, using montelukast sodium after converting it into free acid has been reported (JP 2007-508271). However, a method of improving the hygroscopicity of montelukast sodium using a formulation approach has not been reported yet.

In general, as a method of improving hygroscopic stability of a solid preparation, sugar-coating of a solid preparation and film-coating of a solid preparation with a macromolecular substance have been put to practical use. For the latter film-coating, an aminoalkyl methacrylate copolymer E (Eudragit EPO (registered trademark); Degussa) is known as a macromolecular substance that exhibits moisture barrier properties, and a film coating agent having an improved moisture barrier performance by adding stearic acid to an aminoalkyl methacrylate copolymer E (JP 2004-518750) have been developed.

Even in the case where a solid preparation is not coated directly with a film, there is the case where hygroscopic stability is secured by packaging with packaging materials having high water vapor barrier properties. Examples of such a case include the case where a solid preparation is indirectly protected from moisture by placing the solid preparation in a PTP (press through pack) sheet laminated with polyvinylidene chloride and sealing the sheet.

On the other hand, from the standpoint of preventing forgetting to take prescribed drugs or taking a wrong dose, one-dose packages have been widely used at clinical sites and dispensing pharmacies recently. One-dose packages are provided to patients such that a pharmacist takes out a plurality of solid preparations to be taken in one dose from a packaging material such as a PTP sheet and puts them in one package for each patient. In addition, in western countries, patients often subdivide a pharmaceutical taken out from a package such as a PTP sheet for storage in a pill case or the like, and therefore methods for improving the water vapor barrier properties of a solid preparation itself have been demanded.

However, in one-dose packaging, since each solid preparation will be stored for a long period of time in an automatic packing machine in a naked state as taken out in advance from a packaging material such as a PTP sheet, the protective effect of the packaging material against humidity wears off, and particularly for a solid preparation containing montelukast sodium which has high hygroscopicity as an active ingredient, it is extremely difficult at present to formulate in a one-dose package because of being susceptible to humidity during storage. In other words, patients who receive a preparation containing montelukast sodium as an active ingredient have not gained the advantage of one-dose package that it improves drug compliance to enhance a therapeutic effect and, therefore, there is a need to develop, using a formulation approach, a preparation adaptable to one-dose package containing montelukast sodium as an active ingredient.

Thus, it could be helpful to provide a montelukast-containing coated solid preparation that can be applied to one-dose package, wherein the humidity stability of montelukast or a pharmacologically acceptable salt thereof contained therein is maintained even when the preparation is unpacked.

SUMMARY

We discovered that a coated solid preparation with significantly improved stability to humidity can be obtained by coating a solid preparation containing as an active ingredient montelukast or a pharmacologically acceptable salt thereof with a coating agent containing a particular component in a particular state without increasing the size of the coated solid preparation (without posing any problem in patients' taking the coated solid preparation).

Thus, we provide a coated solid preparation containing as an active ingredient montelukast or a pharmacologically acceptable salt thereof and being coated with a coating layer comprising polyvinyl alcohol and swelling clay, wherein the mass ratio of the above-described polyvinyl alcohol to the above-described swelling clay in the above-described coating layer is 8:2 to 3:7.

In the coating layer of the coated solid preparation described above, the swelling clay has a labyrinth-like structure which has the effect of preventing contact of the solid preparation with water vapor (hereinafter referred to as "labyrinth effect") under the influence of the mass ratio of polyvinyl alcohol to swelling clay and the swollen state of swelling clay. Therefore, the humidity stability of the coated solid preparation and the medicinal ingredient montelukast can be improved, and the delayed disintegration and delayed dissolution of the coated solid preparation caused by moisture absorption can also be prevented. Further, the above-described coated solid preparation exerts a sufficient labyrinth effect even when the coating layer is in the state of a thin film and, therefore, there is no problem in patients' taking the coated solid preparation.

In the above-described coated solid preparation, the above-described swelling clay is preferably dispersed as a laminated structure, and the increase in moisture absorption of the coated solid preparation at 40° C. and a relative humidity of 75% is preferably not more than 3% by mass.

In the coating layer of the coated solid preparation described above, if the swelling clay is dispersed as a laminated structure, the labyrinth effect is strongly exerted and the humidity stability of the coated solid preparation and the medicinal ingredient montelukast can be further improved. Further, when the increase in moisture absorption of the above-described coated solid preparation at room temperature 40° C. and at a relative humidity of 75% is not more than 3% by mass, such a quality stability that there is no problem in handling under a normal room-temperature environment can be maintained for a long period of time, and the delayed disintegration and delayed dissolution can also be stably prevented.

In the above-described coated solid preparation, the above-described swelling clay is preferably bentonite or magnesium aluminum silicate.

Bentonite and magnesium aluminum silicate are able to further improve the humidity stability of the coated solid preparation because they produce a larger labyrinth effect in the coating layer formed on the surface of the solid preparation.

The humidity stability of our coated solid preparation and of montelukast or a pharmacologically acceptable salt thereof contained in the coated solid preparation can be maintained even when the preparation is unpacked. In addition, we provide a montelukast-containing coated solid preparation that can be applied to one-dose package even when the preparation is unpacked, and contributes to improving drug compliance of patients who receive the coated solid preparation to enhance the therapeutic effect. Further, the coated solid preparation is applicable not only to tablets, but also granule preparations.

DETAILED DESCRIPTION

Figure 1:
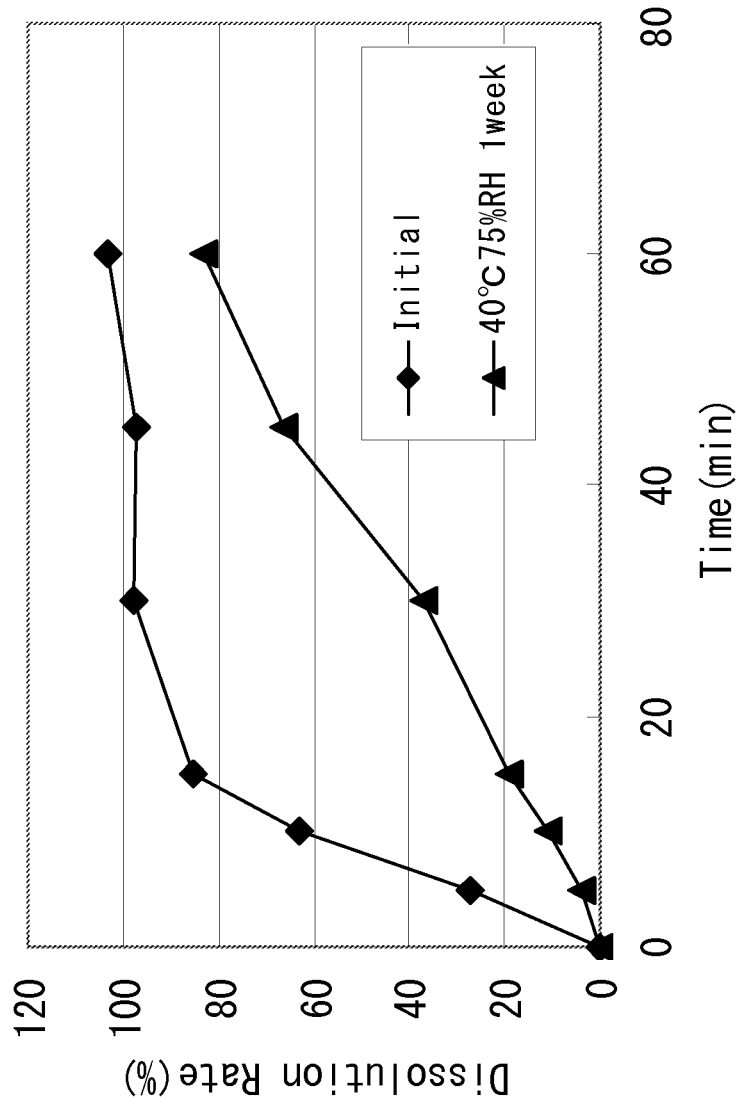
FIG. 1 is a release profile of a Reference Example.

Preferred preparations will now be described. It should be understood, however, that our preparations are not limited to the following examples. Unless otherwise specified, "%" means "% by mass (w/w %)."

The coated solid preparation contains as an active ingredient montelukast or a pharmacologically acceptable salt thereof and being coated with a coating layer comprising polyvinyl alcohol and swelling clay, wherein the mass ratio of the above-described polyvinyl alcohol to the above-described swelling clay in the above-described coating layer is 8:2 to 3:7.

"Solid preparation" refers to a pharmaceutical formulated to be a solid, examples of which include tablets (including sublingual tablets and orally disintegrating tablets), capsules (including soft capsules and microcapsules), granules, fine granules, powders, balls, troches, or filming agents.

"Coated solid preparation" refers to a preparation in which a coating layer is formed to prevent the pharmacologically active components from, for example, being decomposed by oxygen, water vapor, light, and the like by coating the surface of the above-described solid preparation with a coating agent.

Examples of "montelukast or a pharmacologically acceptable salt thereof" include, for example, montelukast or montelukast sodium. Examples of commercially available preparations of montelukast sodium include, for example, Singulair tablets 10 mg (Banyu Pharmaceutical Co., Ltd.), Singulair chewable tablets (Banyu Pharmaceutical Co., Ltd.), Singulair fine granules 4 mg (Banyu Pharmaceutical Co., Ltd.), Kipres tablets (KYORIN Pharmaceutical Co., Ltd.), Kipres chewable tablets (KYORIN Pharmaceutical Co., Ltd.), or Kipres fine granules 4 mg (KYORIN Pharmaceutical Co., Ltd.).

"Polyvinyl alcohol" (hereinafter referred to as "PVA") refers to an alcohol obtained by saponifying polyvinyl acetate, including from partially saponificated PVA having several ten percent of residual acetic acid groups to completely saponificated PVA having only a few percent of residual acetic acid groups.

The saponification degree of PVA is preferably 70 to 97 mol%. The average degree of polymerization of PVA is preferably 200 to 3000 and more preferably 600 to 2400.

The above-described PVA may be used by mixing two or more PVAs having different saponification degree and different average degree of polymerization. When mixing two or more PVAs, for example, it is preferable to add a PVA of high polymerization grade to a PVA of low polymerization grade and mix them.

Examples of PVAs include, for example, various types of Poval (Kuraray Co., Ltd.) or Gohsenol (Nippon Synthetic Chemical Industry Co., Ltd.).

"Swelling clay" refers to clay having swelling properties, and particularly to a substance having swelling properties among finely-powdered substances that exhibit viscosity and plasticity when containing an appropriate amount of water.

As the swelling clay, those that are negatively charged because of the compositional balance of the metal salt species are preferred, examples of which include smectites such as hydrated aluminum silicate having a three-layer structure.

"Negatively charged" refers to the state of the swelling clay's having cation exchange capability, and the amount of charge is expressed as Cation Exchange Capacity (CEC). The unit of cation exchange capacity is milliequivalent/100 grams (hereinafter referred to as "meq/100 g") and generally expressed as the number of equivalents which corresponds to the molar concentration of monovalent ions.

Examples of the above-described smectite include, for example, beidellite, nontronite, saponite, hectorite, sauconite, bentonite (hereinafter referred to as "BT"), magnesium aluminum silicate, or mixtures thereof. BT or magnesium aluminum silicate is preferred, and BT is more preferred.

The above-described swelling clay is preferably dispersed as a laminated structure. "Laminated structure" refers to a laminated structure formed by stacking of a plurality of layer-shaped structures, particularly to a structure in which 10 to 100 layers of the strips of swelling clay are stacked. To disperse the swelling clay as a laminated structure, it is preferable to coat the surface of the solid preparation with a coating agent containing swelling clay in a swollen state.

In the cross section in the thickness direction of the film formed from a coating agent containing swelling clay, strips of the swelling clay are preferably dispersed in a mesh pattern and planarly oriented. The state of the strips of the swelling clay in the cross section in the thickness direction of the film can be observed by using, for example, a transmission electron microscope (TEM).

"In a mesh pattern" refers to the situation where strips of the swelling clay are forming literally a mesh when the dispersion state of the strips of the swelling clay in the cross section in the thickness direction of the film is expressed two-dimensionally.

"Planarly oriented" refers to the situation where the strips of the swelling clay are laminated in the thickness direction of the film.

"Swollen state of swelling clay" refers to the state in which the swelling clay is swollen by containing a dispersion medium. Examples of the swelling clay in a swollen state include, for example, a dispersion obtained by suspending swelling clay in a dispersion medium and stirring the suspension, for example, with a homogenizer, and it is preferable to be dispersed to the extent that all the swelling clay is able to pass through a filter paper when the dispersion is filtered. Examples of the filter paper used in the above-described filtering operation include, for example, No.5B quantitative filter paper (ADVANTEC) and a glass fiber filter paper GF/D (particle holding capacity; 2.7 µm, Whatman).

Examples of dispersion media for a coating agent containing swelling clay, i.e., solvents used in preparation of a coating agent include, for example, water, organic solvents such as lower alcohols having 5 or less carbon atoms, or mixed solvents thereof, among which water is preferred.

To the above-described coating agent, pharmaceutically acceptable additives may be added. To improve dispersibility of the swelling clay, surfactants can be added. To improve disintegration properties of the coated solid preparation, for example, saccharides and sugar alcohols such as maltose, maltitol, sorbitol, xylitol, fructose, glucose, lactitol, isomaltose, lactose, erythritol, mannitol, trehalose, or sucrose; croscarmellose sodium; or low-substituted hydroxypropylcellulose can be added.

To the above-described coating agent, additives generally used for coating in the pharmaceutical field may be further added, and examples of such additives include, for example, coloring agents such as dyes extracted from plants, titanium oxide, calcium carbonate, or silicon dioxide, which serve as a masking agent.

"Coating layer" refers to a layer of a film formed by coating a solid preparation with a coating agent. The coating layer contains PVA and swelling clay, and the mass ratio of the PVA to the swelling clay is 8:2 to 3:7 and preferably 6:4 to 3:7.

The reason is that, when the mass of swelling clay is less than one fourth of the mass of PVA, the labyrinth effect of swelling clay is reduced so that the humidity stability of montelukast or a pharmacologically acceptable salt thereof cannot be sufficiently obtained, and when the mass of swelling clay is above 2.3 times the mass of PVA, the laminated structure of the coating layer becomes non-uniform because of the too high ratio of swelling clay so that the humidity stability of montelukast or a pharmacologically acceptable salt thereof cannot be sufficiently obtained again. The percentage of swelling clay in the above-described coating layer is preferably 5% or more based on the total coating layer.

The increase in moisture absorption of tablets after the above-described coated solid preparation has been stored under the environment of 40° C. and a relative humidity of 75% for 1 week is preferably 3% or less and more preferably 2% or less.

The water vapor transmission of the above-described coating layer is preferably $1.0 \times 10^{-5}$ to $1.0 \times 10^{-4}$ g·mm/cm²·24 hr·atm, more preferably $1.0 \times 10^{-5}$ to $6.0 \times 10^{-5}$ g·mm/cm²·24 hr·atm, and still more preferably $1.0 \times 10^{-5}$ to $3.5 \times 10^{-5}$ g·mm/cm²·24 hr. atm.

The above-described coating layer preferably covers the solid preparation at a mass percentage of 2 to 200% based on the solid preparation, and when the solid preparation is tablets, the mass percentage is preferably 3 to 30%, more preferably 3 to 20%, and still more preferably 3 to 15%.

Examples of the method for coating the surface of the solid preparation with a coating agent include, for example, the use of a coating pan or a coating machine for tablets in the case where the solid preparation is in the form of tablets and, for example, the use of a fluidized-bed coating machine or a rolling fluidized-bed coating machine in the case where the solid preparation is in the form of granules or powders.

The above-described coated solid preparation may be further coated with a functional film, for example, of gastric-soluble or enteric-soluble macromolecular substances. Further, the inner side of the coating layer containing PVA and swelling clay may be coated in advance with a functional film, for example, of gastric-soluble or enteric-soluble macromolecular substances.

EXAMPLES

Our preparations will now be specifically described by way of examples, but this disclosure is not limited thereto.

Reference Example

For the tablets obtained by storing montelukast sodium tablets (Singulair tablets 10 mg; Banyu Pharmaceutical Co., Ltd.) for 1 week under conditions of 40° C. and at a relative humidity of 75% (hereinafter referred to as "1-week stored tablets at 40° C. and 75% RH"), dissolution tests and measurements of disintegration time were performed. The dissolution tests were carried out in accordance with the Japanese Pharmacopoeia, 15th Edition, Dissolution Test, Second Method. The tablets were placed into a 900 mL of a test solution obtained by adding polysorbate 80 of 0.5% concentration to distilled water, and dissolved solutions were collected over time for a quantitative determination under the HPLC conditions below. The release profile is shown in FIG. 1.

HPLC Conditions

Mobile phase: acetate buffer (pH 3.5)/methanol=15/85 (v/v)

Column: Hypersil ODS (4.6×250 mm)

Detection wavelength: 254 nm

It is clear from the release profile shown in FIG. 1 that the 1-week stored tablets at 40° C. and 75% RH exhibit significantly delayed dissolution compared to montelukast sodium tablets before storage (hereinafter referred to as "pre-storage tablets"). Also for disintegration time, the disintegration time of the pre-storage tablets is within 10 minutes, whereas the disintegration time of the 1-week stored tablets at 40° C. and 75% RH reached as long as 40 minutes. The conditions of storage at 40° C. and a relative humidity of 75% for 1 week can be considered as further accelerated conditions of the conditions of storage at 85% RH for 4 weeks reported in the prior art reference (Nishioka et al.). Thus, as described below, the tablets after storage at 40° C. and at a relative humidity of 75% for 1 week were evaluated for an increase in moisture absorption and disintegration delay time to thereby confirm the excellent effect. Method for calculating increase in moisture absorption The mass of the pre-storage tablets and the post-storage tablets were measured, and the increase in moisture absorption was calculated by Equation 1 below:

$$\text{Increase in moisture absorption (\% by mass)} = ((W-Ws)/Ws) \times 100 \quad \text{Equation 1}$$

W: Mass of post-storage tablets (g)
Ws: Mass of pre-storage tablets (g).

Method of measuring disintegration time

Disintegration tests were performed in accordance with Japanese Pharmacopoeia, 15th Edition, Disintegration Test, to measure disintegration time. Specifically, using distilled water as a test solution, the time until tablets lose their shape under conditions of a stroke of 30 times/min was taken as the disintegration time.

Method for Calculating Disintegration Delay Time

The disintegration time of the pre-storage tablets and post-storage tablets were measured, and the disintegration delay time was calculated by Equation 2 below:

$$\text{Disintegration delay time (min)} = T - Ts \quad \text{Equation 2}$$

T: Disintegration time of post-storage tablets (min)
Ts: Disintegration time of pre-storage tablets (min).

Method of Measuring Water Vapor Transmission

Measurement of the water vapor transmission of the coating layer constituting the coated solid preparation was performed in accordance with JIS K 8123 (1994) with minor modifications.

Specifically, a film of a coating layer formed with a coating agent prepared as appropriate was cut, with light passing therethrough, selectively at a portion of uniform thickness without a pinhole into a circle with a diameter of 3.5 cm, and the thickness of the film was measured at arbitrary five points.

Next, 3 g of calcium chloride (particle size: 850 to 2000 μm) was placed in an aluminum cup (diameter: 30 mm), and the film of a coating layer cut into a circle and a ring for fixing the film were sequentially placed on the aluminum cup. The ring was fixed by placing a weight on the ring, and in this state, molten paraffin wax was poured into the edge of the aluminum cup. After the paraffin wax was solidified, the weight was removed, and the mass of the whole aluminum cup was measured to determine the initial mass. Then, the aluminum cup was placed in a thermostat bath at 40° C. and 75% RH. The aluminum cup was taken out every 24 hours for measuring the mass to calculate the water vapor transmission coefficient by using Equation 3 below. In all of the tests for measuring the water vapor transmission described below, r=1.5 cm; t=24 hours; and C=1 atm.

$$\text{Water vapor transmission } P \text{ (g·mm/cm}^2 \cdot 24 \text{ hr·atm)} = W \times A / B \times t \times C \quad \text{Equation 3}$$

W: Mass increased in 24 hours (g)
A: Average value of film thickness at five points (mm)
B: Transmission area $\pi r^2$ (cm$^2$)
t: Elapsed time (hr)
C: Atmospheric pressure (atm)

Example 1

To 234.6 parts by mass of water, added were 6.9 parts by mass of PVA (EG-05; Nippon Synthetic Chemical Industry Co., Ltd.), 505.3 parts by mass of a 3.2% BT solution, and 3.2 parts by mass of sorbitan monolaurate (hereinafter referred to as "Span 20"), and the resulting mixture was stirred with a homogenizer (Polytron Model KR) to obtain a coating agent (hereinafter referred to as "Example 1 coating agent"). As a 3.2% BT solution, used was a filtrate obtained by adding 32 parts by mass of BT (Kunipia-F; KUNIMINE INDUSTRIES CO., LTD., cation exchange capability: 115 meq/100 g) to 968 parts by mass of stirred water, stirring the resulting mixture with the homogenizer for uniform dispersion, and then suction-filtering the resultant through a filter paper.

Twenty grams of montelukast sodium tablets (Singulair tablets 10 mg; Banyu Pharmaceutical Co., Ltd.) and 280 g of placebo tablets were placed in a coating pan (HI-COATER MINI; Freund Industrial Co., Ltd.), and Example 1 coating agent was applied to the tablets until the thickness of the coating layer reached 50 to 60 μm. For the coated montelukast sodium tablets obtained, the increase in moisture absorption and the disintegration delay time after storage for 1 week under conditions of 40° C. and a relative humidity of 75% were calculated.

Example 1 coating agent was sprayed onto the back of a polypropylene balance tray, and immediately dried with hot air from a dryer. After repeating these operations several times, the balance tray was allowed to stand in an oven at 50° C. and dried overnight, and a film was separated from the balance tray to measure the water vapor transmission.

Example 2

From a coating agent obtained by adding 14.0 parts by mass of PVA and 656.2 parts by mass of a 3.2% BT solution to 329.8 parts by mass of water and stirring the resulting mixture with a homogenizer, a film was produced in the same manner as in Example 1, and the water vapor transmission was measured.

Example 3

Using a coating agent obtained by adding 20.0 parts by mass of PVA and 625.0 parts by mass of a 3.2% BT solution to 355.0 parts by mass of water and stirring the resulting mixture with a homogenizer, coated montelukast sodium tablets was obtained in the same manner as in Example 1, and the increase in moisture absorption after storage for 1 week under conditions of 40° C. and at a relative humidity of 75% RH was calculated. Further, a film was produced from the coating agent in the same manner as in Example 1, and the water vapor transmission was measured.

Example 4

Using a coating agent obtained by adding 21.0 parts by mass of PVA and 437.5 parts by mass of a 3.2% BT solution to 541.5 parts by mass of water and stirring the resulting mixture with a homogenizer, coated montelukast sodium tablets was obtained in the same manner as in Example 1, and the increase in moisture absorption after storage for 1 week under conditions of 40° C. and at a relative humidity of 75% RH was calculated. Further, a film was produced from the coating agent in the same manner as in Example 1, and the water vapor transmission was measured.

Example 5

Using a coating agent obtained by adding 32.0 parts by mass of PVA and 250.0 parts by mass of a 3.2% BT solution to 718.0 parts by mass of water and stirring the resulting mixture with a homogenizer, coated montelukast sodium tablets was obtained in the same manner as in Example 1, and the increase in moisture absorption after storage for 1 week under conditions of 40° C. and at a relative humidity of 75% RH was calculated. Further, a film was produced in the same manner as in Example 1, and the water vapor transmission was measured.

Example 6

To 234.6 parts by mass of water, added were 6.9 parts by mass of PVA, 505.3 parts by mass of a 3.2% magnesium aluminum silicate solution, and 3.2 parts by mass of Span 20, and the resulting mixture was stirred with a homogenizer to prepare a coating agent. A film was produced in the same manner as in Example 1, and the water vapor transmission was measured. As a 3.2% magnesium aluminum silicate solution, used was a filtrate obtained by adding 32 parts by mass of magnesium aluminum silicate (Veegum-HV; R.T. Vanderbilt Company, Inc.) to 968 parts by mass of stirred water, stirring the resulting mixture with the homogenizer for uniform dispersion, and then suction-filtering the resultant through a filter paper.

Comparative Example 1

The increase in moisture absorption and the disintegration delay time after montelukast sodium tablets (Singulair tablets 10 mg; Banyu Pharmaceutical Co., Ltd.) have been stored for 1 week under conditions of 40° C. and at a relative humidity of 75% were calculated.

Comparative Example 2

Using a coating agent obtained by adding 7.0 parts by mass of PVA and 875.0 parts by mass of a 3.2% BT solution to 118.0 parts by mass of water and stirring the resulting mixture with a homogenizer, coated montelukast sodium tablets was obtained in the same manner as in Example 1, and the increase in moisture absorption after storage for 1 week under conditions of 40° C. and at a relative humidity of 75% was calculated. Further, a film was produced from the coating agent obtained in the same manner as in Example 1, and the water vapor transmission was measured.

Comparative Example 3

Using a coating agent obtained by adding 36.0 parts by mass of PVA and 125.0 parts by mass of a 3.2% BT solution to 839.0 parts by mass of water and stirring the resulting mixture with a homogenizer, coated montelukast sodium tablets was obtained in the same manner as in Example 1, and the increase in moisture absorption after storage for 1 week under conditions of 40° C. and at a relative humidity of 75% was calculated. Further, a film was produced from the coating agent obtained in the same manner as in Example 1, and the water vapor transmission was measured.

Comparative Example 4

From a coating agent obtained by adding 3.0 parts by mass of PVA and 843.8 parts by mass of a 3.2% BT solution to 153.2 parts by mass of water and stirring the resulting mixture with a homogenizer, a film was produced in the same manner as in Example 1, and the water vapor transmission was measured.

The mass ratio of PVA to BT to the third component contained in each coating agent of Examples 1 to 6 and Comparative Examples 1 to 4, the increase in moisture absorption calculated in Examples 1, 3 to 5 and Comparative Examples 1 to 3, and the water vapor transmission measured in Examples 1 to 6 and Comparative Examples 2 to 4 are shown in Table 1.

TABLE 1

|  | PVA | Swelling clay | Third component | 1-week storage Increase in moisture absorption (% by mass) | Water vapor transmission of film (g · mm/cm$^2$ · 24 hr · atm) |
| --- | --- | --- | --- | --- | --- |
| Comparative Example 1 | — | — | — | 3.9 | — |
| Comparative Example 2 | 20 | 80 | — | 3.8 | $1.4 \times 10^{-4}$ |
| Comparative Example 3 | 90 | 10 | — | 3.3 | $2.3 \times 10^{-4}$ |
| Comparative Example 4 | 10 | 90 | — | — | $6.2 \times 10^{-4}$ |
| Example 1 | 26.4 | 61.6 | 12 | 1.1 | $1.9 \times 10^{-5}$ |
| Example 2 | 40 | 60 | — | — | $3.4 \times 10^{-5}$ |
| Example 3 | 50 | 50 | — | 1.4 | $2.5 \times 10^{-5}$ |
| Example 4 | 60 | 40 | — | 2.4 | $3.2 \times 10^{-5}$ |
| Example 5 | 80 | 20 | — | 2.9 | $5.8 \times 10^{-5}$ |
| Example 6 | 30 | 70 | — | — | $9.1 \times 10^{-5}$ |

From the results in Table 1, it is clear that when the mass ratio of PVA to swelling clay is in the range of 8:2 to 3:7, the increase in moisture absorption of the montelukast sodium tablets is not more than 3.0% by mass, and the water vapor transmission of the film is not more than $1.0 \times 10^{-4}$. Therefore, the coated solid preparation is very stable to humidity.

Further, the disintegration delay time in Comparative Example 1 is 30 minutes, whereas the disintegration delay time in Example 1 is 4 minutes. Also from these results, it is clear that the disintegration delay time of the coated solid preparation is significantly short, and the disintegration performance can be maintained even if the preparation has been stored under a high humidity environment.

Measurement of Films Under Transmission Electron Microscope

Using the focused ion beam technique, the longitudinal section of each film obtained in Examples 1 to 3 and Comparative Examples 3 and 4 was observed under a transmission electron microscope. The micrograph of Example 1, the micrograph of Example 2, the micrograph of Example 3, the micrograph of Comparative Example 3, and the micrograph of Comparative Example 4 are shown in FIG. 2, FIG. 3, FIG. 4, FIG. 5 and FIG. 6, respectively.

Figure 2:
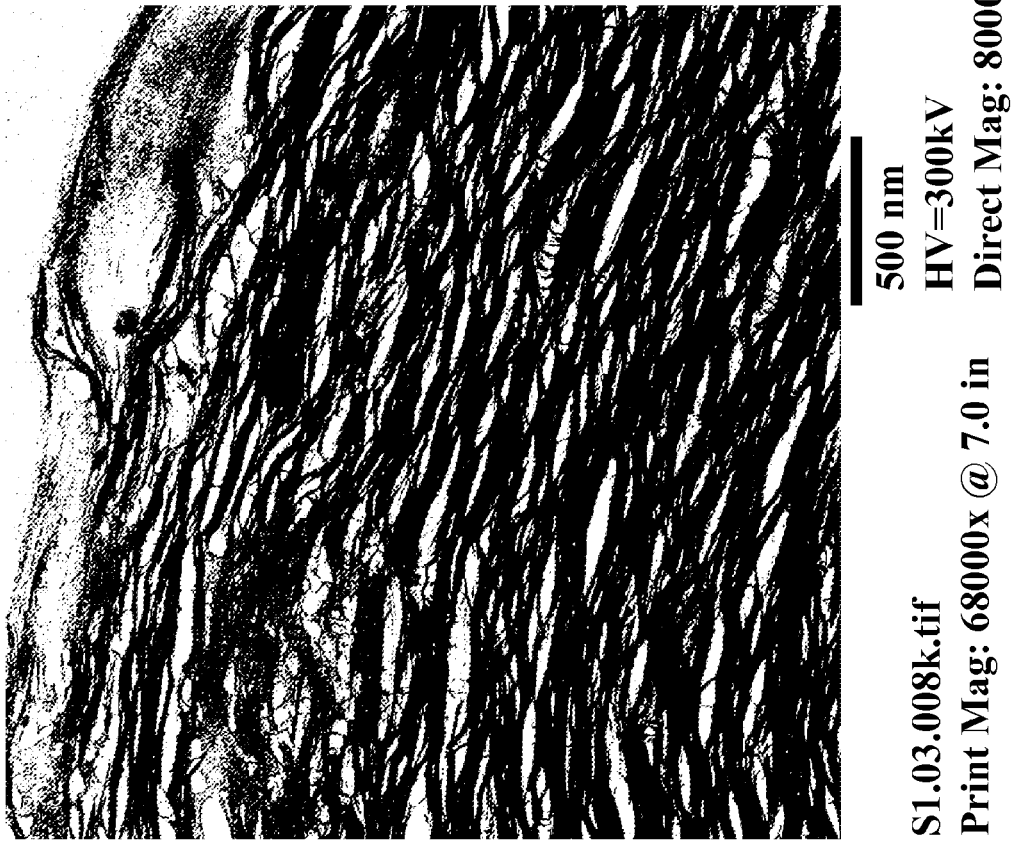
FIG. 2 is a focused ion beam transmission electron micrograph of the film of Example 1.
Figure 3:
FIG. 3 is a focused ion beam transmission electron micrograph of the film of Example 2.
Figure 4:
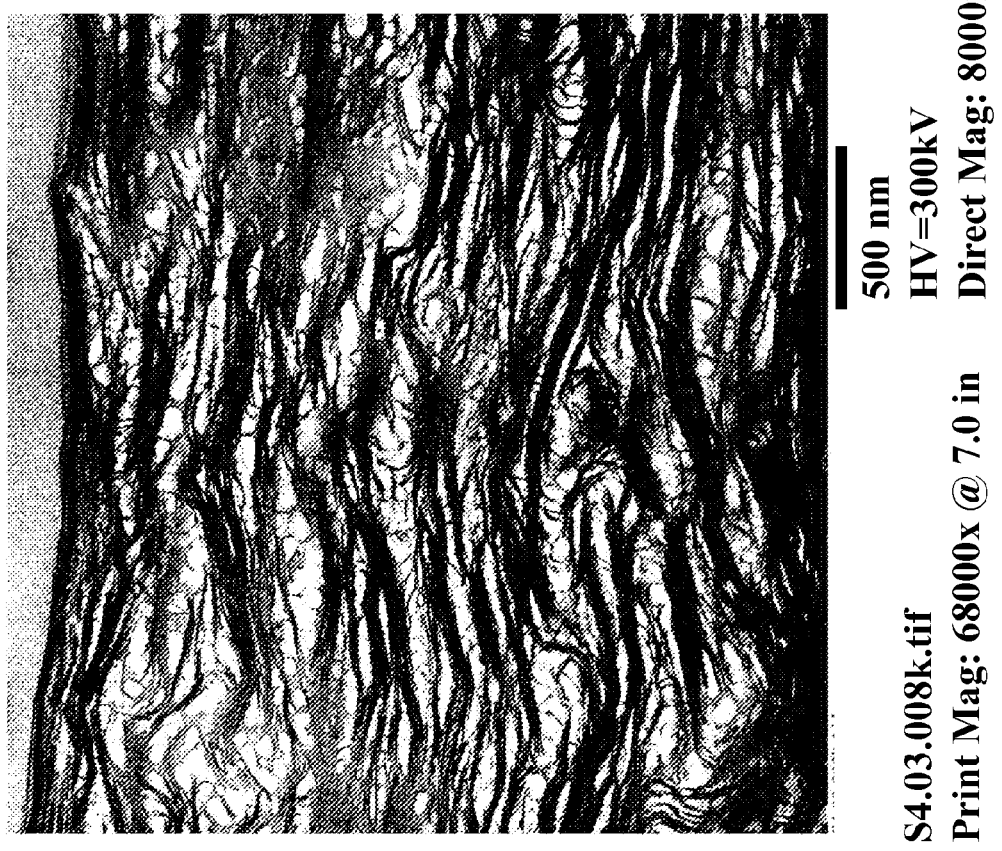
FIG. 4 is a focused ion beam transmission electron micrograph of the film of Example 3.
Figure 5:
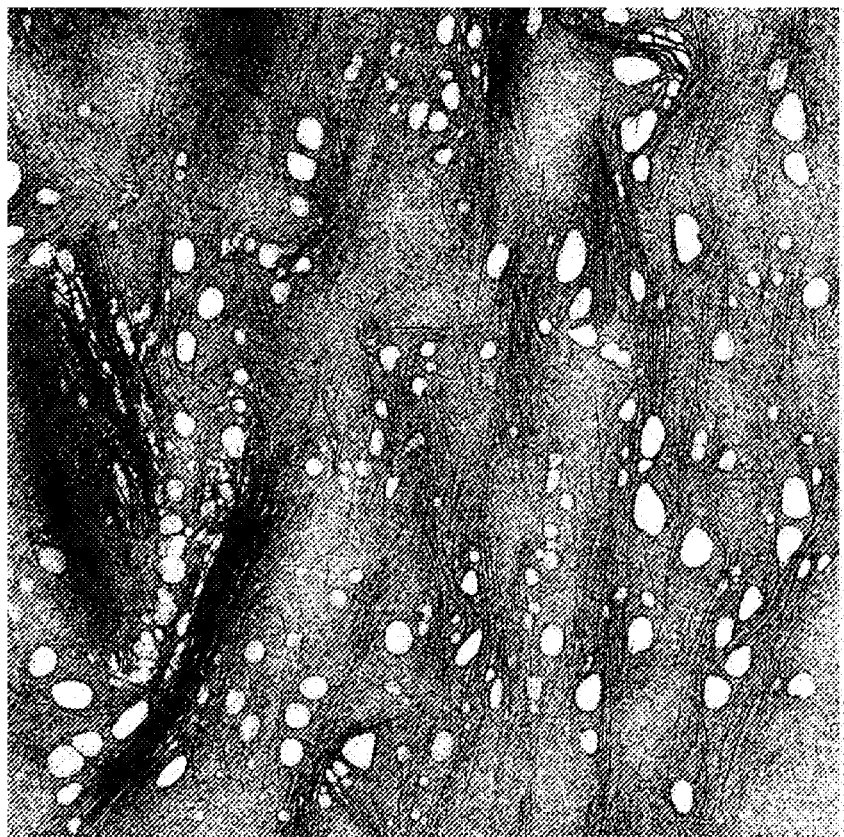
FIG. 5 is a focused ion beam transmission electron micrograph of the film of Comparative Example 3.
Figure 6:
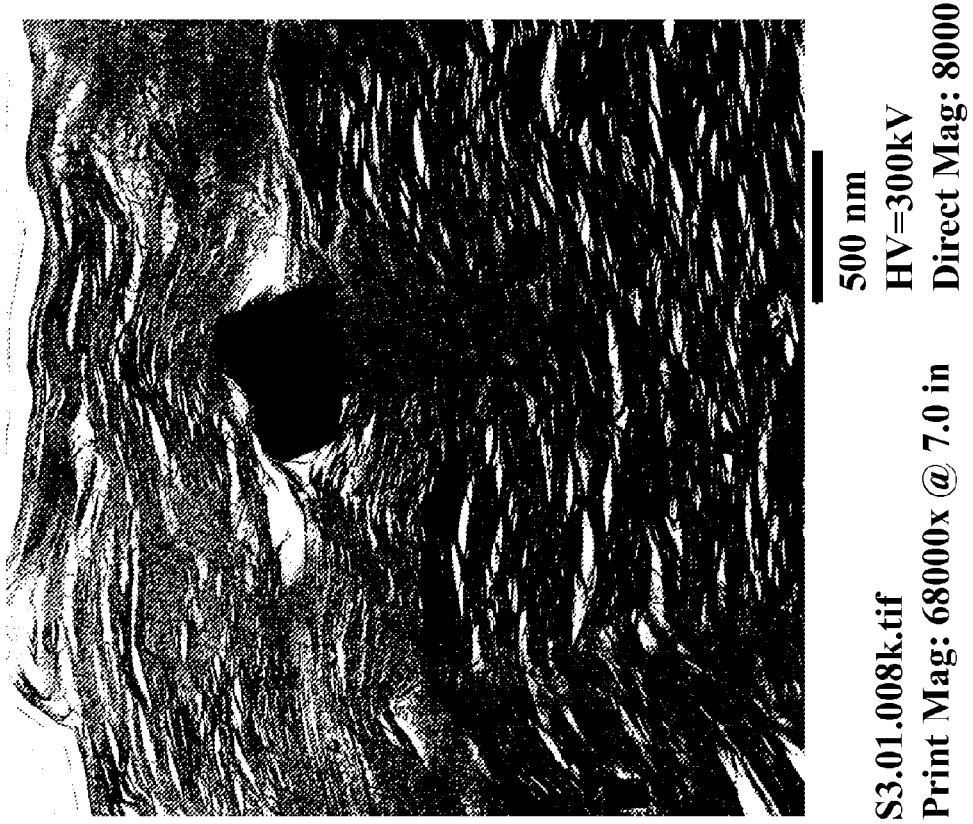
FIG. 6 is a focused ion beam transmission electron micrograph of the film of Comparative Example 4.

In the micrographs of FIGS. 2 to 4, BT was uniformly dispersed as a laminated structure in the film, but in FIG. 5, BT formed little or no laminated structure. Also in FIG. 6, areas where BT is not planarly oriented are found here and there. From the observations above, it is presumed that the uniform dispersion of the laminated structure of BT significantly contributes to the water vapor transmission of the film and the humidity stability of solid preparations such as montelukast sodium tablets.

Comparative Example 5

From a coating agent obtained by adding 16.0 parts by mass of PVA and 4.0 parts by mass of BT to 480.0 parts by mass of water and stirring the resulting mixture with a magnetic stirrer for 15 minutes, a film was produced in the same manner as in Example 1, and the water vapor transmission was measured.

Example 7

Using a coating agent obtained by adding 6.9 parts by mass of PVA, 505.3 parts by mass of a 3.2% BT solution, 3.2 parts by mass of Span 20, and 3.94 parts by mass of maltitol to 343.5 parts by mass of water and stirring the resulting mixture with a homogenizer, coated montelukast sodium tablets was obtained in the same manner as in Example 1, and the increase in moisture absorption after storage for 1 week under conditions of 40° C. and at a relative humidity of 75% was calculated. Further, a film was produced in the same manner as in Example 1, and the water vapor transmission was measured.

The increase in moisture absorption and the water vapor transmission measured and calculated in Examples 1 and 7 and Comparative Example 5 are shown in Table 2.

TABLE 2

|  | Composition | Increase in moisture absorption (% by mass) 1-week storage | Water vapor transmission of film (g · mm/ cm$^2$ · 24 hr · atm) |
|---|---|---|---|
| Example 1 | PVA/BT/Span 20 = 26.4/61.6/12 | 1.1 | $1.9 \times 10^{-5}$ |
| Example 7 | PVA/BT/Span 20/ Maltitol = 23/53.6/10.4/13 | 2.8 | $3.7 \times 10^{-5}$ |
| Comparative Example 5 | PVA/BT = 8/2 | — | $2.7 \times 10^{-4}$ |

The results in Table 2 show that, in both the case where a nonionic surfactant was added to PVA and BT (Example 1) and the case where sugar alcohol was further added (Example 7), the increase in moisture absorption was not more than 3% by mass, and the water vapor transmission of the film was not more than $1.0 \times 10^{-4}$.

The comparison of Example 5 and Comparative Example 5 showed that BT is preferably added not as a powder but in a swollen state.

Industrial Applicability

The coated solid preparation can be suitably used as a pharmaceutical applicable to one-dose package.

The invention claimed is:

1. A coated solid preparation comprising:
   a solid preparation comprising montelukast or a pharmacologically acceptable salt thereof as an active ingredient and a coating layer comprising polyvinyl alcohol and smectite swelling clay coating the solid preparation;
   wherein the mass ratio of said polyvinyl alcohol to said swelling clay in said coating layer is 8:2 to 3:7 and said swelling clay in the coating layer is uniformly dispersed as a laminated structure and strips of the swelling clay are dispersed in a mesh pattern and planarly oriented.

2. The coated solid preparation according to claim 1, wherein an increase in moisture absorption of the coated solid preparation at 40° C. and at a relative humidity of 75% is not more than 3% by mass.

3. The coated solid preparation according to claim 1, wherein said swelling clay is bentonite or magnesium aluminum silicate.

4. The coated solid preparation according to claim 2, wherein said swelling clay is bentonite or magnesium aluminum silicate.

* * * * *